(12) United States Patent
Papadimitriou

(10) Patent No.: US 6,207,718 B1
(45) Date of Patent: Mar. 27, 2001

(54) PHARMACEUTICAL COMPOSITIONS CONTAINING HEDGEHOG PROTEIN

(75) Inventor: Apollon Papadimitriou, Bichl (DE)

(73) Assignee: Ontogeny, Inc., Cambridge, MA (US)

( * ) Notice: Subject to any disclaimer, the term of this patent is extended or adjusted under 35 U.S.C. 154(b) by 0 days.

(21) Appl. No.: 09/365,948

(22) Filed: Aug. 2, 1999

(30) Foreign Application Priority Data

Aug. 7, 1998 (EP) .................................. 98114851
Sep. 3, 1998 (EP) .................................. 98116734

(51) Int. Cl.[7] ........................... A61K 47/30; A61K 9/64; A61K 9/14; A61F 13/00

(52) U.S. Cl. ...................... 514/772.3; 424/422; 424/461; 424/484; 424/486

(58) Field of Search .................. 514/772.3; 424/422, 424/461, 484, 486

(56) References Cited

U.S. PATENT DOCUMENTS

| | | |
|---|---|---|
| 4,614,794 | 9/1986 | Easton et al. . |
| 4,853,226 | 8/1989 | Machida et al. . |
| 5,078,997 | 1/1992 | Hora et al. . |
| 5,156,623 | 10/1992 | Hakamatsuka et al. . |
| 5,416,071 | 5/1995 | Igari et al. . |
| 5,503,827 | 4/1996 | Woog et al. . |
| 5,789,543 | 8/1998 | Ingham et al. . |

FOREIGN PATENT DOCUMENTS

| | | |
|---|---|---|
| 0 531 611 | 3/1993 | (EP) . |
| 0 947 201 | 10/1999 | (EP) . |
| 0 953 575 | 11/1999 | (EP) . |
| 0 953 576 | 11/1999 | (EP) . |
| WO 98/08851 | 8/1990 | (WO) . |
| WO 90/11757 | 10/1990 | (WO) . |
| WO 95/18856 | 7/1995 | (WO) . |
| WO 95/23223 | 8/1995 | (WO) . |
| WO 98/30234 | 7/1998 | (WO) . |
| 98/30234 * | 7/1998 | (WO) . |
| WO 98/46211 | 10/1998 | (WO) . |

OTHER PUBLICATIONS

López–Martinez, Limb–patterning activity and restricted posterior localization of the amino–terminal product of Sonic hedgehog cleavage, Current Biology, vol. 5, pp. 791–796 (1995).

Hall, et al., 1 VHH, Signalling Protein, Available from Internet:<URL:http//www.pdb.bnl.gov/pdb–bin/pdbids?id=1vhh>(1995).

Yang, et al., Relationship between dose, distance and time in Sonic Hedgehog–mediated regulation of anteroposterior polarity in the chick limb, Development 124, pp. 4393–4404 (1997).

Marti, et al., Requirement of 19K form of Sonic hedgehog for induction of distinct of ventral cell types in CNS explants, Nature, vol. 375, pp. 322–325 (1995).

Kikuchi, et al., Pulsed dextran release from calcium–alginate gel beads, Journal of Controlled Release, vol. 47, pp. 21–29 (1997).

Downs, et al., Calcium Alginate Beads as a Slow–Release System for Delivering Angiogenic Molecules In Vivo and In Vitro, J. Cell. Physiol. vol. 152, pp. 422–429 (1992).

Gray, C. J. et al., Retention of Insulin in Alginate Gel Beads, Biotechnol. Bioeng. vol. 31, pp. 607–612 (1988).

López–Martinez, Limb–patterning activity and restricted posterior localization of the amino–terminal product of Sonic hedgehog cleavage, Current Biology, vol. 5, pp. 791–796 (1995).

Hall, et al., 1 VHH, Signalling Protein, Available from Internet:<URL:http//www.pdb.bnl.gov/pdb–bin/pdbids?id=1 vhh>(1995).

Abstract for Document B9.

* cited by examiner

*Primary Examiner*—Thurman K. Page
(74) *Attorney, Agent, or Firm*—Foley, Hoag & Eliot LLP; Matthew P. Vincent

(57) ABSTRACT

A composition of a hedgehog protein which includes as an additive cyclodextrin, a non-ionic detergent, an anionic saccharide and/or ionic salt containing zinc ions, magnesium ions, calcium ions and/or sulfate ions is especially stable at room temperature.

19 Claims, No Drawings

PHARMACEUTICAL COMPOSITIONS CONTAINING HEDGEHOG PROTEIN

BACKGROUND OF THE INVENTION

The invention concerns a composition, preferably a pharmaceutical composition, of hedgehog proteins and its use.

Hedgehog (hh) proteins are understood as a family of secreted signal proteins which are responsible for the formation of numerous structures in embryogenesis (J. C. Smith, Cell 76 (1994) 193–196, N. Perrimon, Cell 80 (1995) 517–520, C. Chiang et al., Nature 83 (1996) 407, M. J. Bitgood et al., Curr. Biol. 6 (1996) 298–304, A. Vortkamp et al., Science 273 (1996) 613, C. J. Lai et al., Development 121 (1995) 2349). During its biosynthesis a 20 kDa N-terminal domain and a 25 kDa C-terminal domain are obtained after cleavage of the signal sequence and autocatalytic cleavage. In its natural form the N-terminal domain is modified with cholesterol or palmitoyl (J. A. Porter et al., Science 274 (1996) 255–259, Pepinski et al., J. Biol.Chem. 273 (1998) 14037–14045). In higher life-forms the hh family is composed of at least three members namely sonic, indian and desert hh (shh, ihh, dhh; M. Fietz et al., Development (Suppl.) (1994) 43–51). Differences in the activity of hedgehog proteins that were produced recombinantly were observed after production in prokaryotes and eukaryotes (M. Hynes et al., Neuron 15 (1995) 35–44 and T. Nakamura et al., Biochem. Biophys. Res. Comm. 237 (1997) 465–469).

Hynes et al. compare the activity of hh in the supernatant of transformed human embryonic kidney 293 cells (eukaryotic hh) with hh produced from *E. coli* and find a four-fold higher activity of hh from the supernatants of the kidney cell line. The reason for this increased activity has been discussed to be a potential additional accessory factor which is only expressed in eukaryotic cells, a post-translational modification, a different N-terminus since the hh isolated from E. coli contains 50% of a hh form which carries two additional N-terminal amino acids (Gly-Ser) or is shortened by 5–6 amino acids, or a higher state of aggregation (e.g. by binding to nickel agarose beads).

Nakamura et al. compare the activity of shh in the supernatant of transformed chicken embryo fibroblasts with an shh fusion protein isolated from *E. coli* which still has an N-terminal polyhistidine part. The shh in the supernatant of the fibroblasts has a seven-fold higher activity than the purified *E. coli* protein with regard to stimulation of alkaline phosphatase (AP) in C3H10T ½ cells. The increased activity has been postulated to be due to molecules such as for example bone morphogenetic proteins (BMPs) which are only present in the supernatant of eukaryotic cells and cause the stronger induction of AP.

Pepinski et al. (J. Biol. Chem. 273 (1998) 14037–14045) have identified a shh form which is modified with palmitic acid. This shh mutant is 30-fold more potent than the unmodified form in the C3H10T ½ assay.

Kinto et al., FEBS Letters, 404 (1997) 319–323 described that fibroblasts which secrete hh induce ectopic bone formation in an i.m. implantation on collagen. Thus hedgehog proteins have an osteoinductive activity. Hedgehog proteins can also stimulate the formation of cartilage cells (Stott et al., 1997).

It is known from Yang et al., Development 124 (1997) 4393–4404 that high local hedgehog concentrations must prevail over a period of at least 16 h at the site of action in the body for a pharmaceutically effective in vivo activity. The carrier system described by Yang et al. i.e. the hedgehog-loaded chromatography medium Affigel CM, the Ni agarose described by Marti et al., in Nature 375 (1995) 322–325 or the Affigel blue used by Lopez-Martinez et al., in Curr.Biol. 5 (1995) 791–796 or the heparin agarose particles that they used are less suitable for a pharmaceutical application since they are immunogenic and can cause inflammatory reactions.

SUMMARY OF THE INVENTION

The object of the present invention is to provide a stable, preferably aqueous (preferably pharmaceutical) composition of a hedgehog protein.

The object is achieved by a, preferably pharmaceutical, composition of a hedgehog protein which contains a hedgehog protein in a pharmaceutically effective amount and, an additive being present in an effective amount to stabilize said hedgehog protein. The additive is preferably selected from the group consisting of ionic salts, cyclodextrin, non-ionic detergent, anionic saccharide and mixtures thereof. Preferred ionic salts are those containing an ion selected from the group consisting of zinc, sulfur, magesium, calcium, arginine, argininium and mixtures thereof.

In accordance with the present invention, compositions are provided which stabilize hedgehog proteins and allow the activity of the hedgehog protein to be maintained over a long period for example at room temperature. Thus, the compositions of the present invention allow for longer storage of pharmaceutically effective hedgehog protein compositions prior to administration to a patient. The compositions described herein are also particularly suitable for producing carrier matrices containing a pharmaceutically effective amount of hedgehog protein. The carrier matrices produced from the compositions of the present invention can be administered to a human patient to provide delayed release of pharmaceutically effective hedgehog protein in the human body.

DETAILED DESCRIPTION OF THE INVENTION

It has surprisingly turned out that one or several additives selected from the group ionic salts, cyclodextrin, non-ionic detergents and anionic saccharides such as chondroitin sulfate or heparin are able to stabilize hedgehog proteins (as a pharmaceutical composition or in another form), preferably in an aqueous solution. As a result the activity of the hedgehog protein can be maintained over a long period for example at room temperature and the compositions of hedgehog proteins can be stored in suitable containers, such as, vials, for a long period at room temperature prior to administration to a human patient in unit dosage form. The additives according to the invention are also suitable for stabilizing hedgehog lyophilisates (preferably as a bulk or pharmaceutical composition) and also stabilize the hedgehog proteins during the production of hedgehog preparations such as implants, microparticles, gels etc. and at increased temperatures (e.g. 37° C.).

In accordance with the present invention a composition is provided comprising an aqueous solution containing a hedgehog protein and an additive being present in an effective amount to stabilize said hedgehog protein, wherein said additive is selected from the group consisting of ionic salts, cyclodextrin, non-ionic detergent, anionic saccharide and mixtures thereof, said ionic salt containing an ion selected from the group consisting of zinc, sulfur, magesium, calcium, arginine, argininium and mixtures thereof.

In the aqueous solution of the hedgehog protein according to the invention the additive is in a molar excess relative to the hedgehog proteins. This excess is preferably 1–1000-fold and particularly preferably 1–100-fold. The aqueous solution according to the invention is especially suitable for producing combinations of hedgehog proteins with carrier substances.

Hence a further subject matter of the invention is an aqueous solution of a hedgehog protein which is characterized in that it contains a molar excess of the additive according to the invention relative to the hedgehog protein. The aqueous solution is preferably buffered and/or lyophilized. The composition of the present invention is adapted for formulating unit dosage forms for administration to a patient. Parenteral administration of the composition to a patient is preferred. The amount of the aqueous solution administered to a human patient in unit dosage form is from about 0.05 ml to about 2.0 ml, preferably, from about 0.5 ml to about 2.0 ml.

The amount of additives according to the invention is per se uncritical and can be varied over a wide range. Suitable amounts depend on the pharmaceutical compatibility of the additive and the extent of the stabilizing action at a pharmaceutically acceptable concentration. Ionic salts are added at a concentration of from about 0.01 mmol to about 500 mmol/l. Zinc ions are particularly preferred as a stabilizer and can for example be advantageously added at a concentration of 0.01–100 mmol/l. This concentration has a significant stabilizing effect on hedgehog proteins. Zinc ions are preferably added at pharmaceutically compatible doses. Preferred ionic salts containing zinc are zinc sulfate and zinc acetate.

Cyclodextrin can be preferably present according to the invention as cyclodextrin sulfate. The concentrations are preferably between 1 and 20% by weight. Sulfated β-cyclodextrin is especially preferred. Low molecular weight heparin (ca. 3 kDa) is preferably used as an anionic polysaccharide. The concentration is preferably 0.5–50 mg/ml for low molecular weight heparin and corresponding molar amounts are used for high molecular weight heparin. Sulfate ions are preferably added as zinc sulfate. The sulfate ion concentration is preferably 0.01–100 mmol/l. Calcium and magnesium ions are preferably used at a concentration of 0.01–100 mmol/l. Calcium and magnesium ions are preferably added to the compositions of the present invention as calcium acetate and magnesium acetate. Preferred ionic salts containing arginine or argininium are arginine chloride, arginine sulfate, argininium chloride and argininium sulfate. Non-ionic detergents are preferably polyoxysorbates (e.g. Tween®20, Tween®80), preferably at a concentration of 0.01 to 0.1% (w/v)).

The hedgehog protein is preferably present on a biocompatible carrier in which case the carrier binds the hedgehog protein in its active, folded structure and can locally release hedgehog protein in vivo in its active form and in a delayed manner. Such formulations are particularly suitable for the repair of cartilage defects, but can also be used to repair neuronal defects or for a systemic delivery.

In a preferred embodiment the composition, and preferably the pharmaceutical composition, contains the hedgehog protein bound to a hydrophilic carrier which is biocompatible and can for example be used as an implant. The carrier is preferably a polymer which binds the hedgehog protein as a negatively charged carrier as a result of ionic interactions, the hedgehog protein is not denatured when it is bound to the carrier, the carrier contains at least 0.1 to 1, preferably 0.1 to 2 negatively charged residues per monomer under neutral conditions, the charge is mediated in the form of acidic groups such as sulfate, carboxyl or phosphate groups, and the average molecular weight of the carrier is at least 50,000 Da.

It has turned out that hedgehog proteins can be reversibly and actively released in vivo from a carrier in a delayed manner when they are bound to a negatively charged, soluble or insoluble polymer matrix. Such carrier matrices are for example described in the European Patent Application No. 98104416.7. Preferred carriers are polysaccharides such as hyaluronic acid, sodium alginate and dextran sulfate.

A pharmaceutical effect is preferably understood as a neurological effect on nerve cells, as osteogenesis and/or osteoinduction, and especially preferably as chondrogenesis and/or chondroinduction as described by Stott et al., in J. Cell Sci. 110 (1997) 2691–2701 for cartilage cell induction, in Kinto et al., FEBS Letters, 404 (1997) 319–323 for bone induction, and by Miao et al. in J. Neurosci. 17 (1997) 5891–5899 for the effect on nerve cells.

Solutions of hedgehog proteins at high concentrations are required to produce carrier matrices that are coated with hedgehog proteins in such a manner that they exhibit an adequate pharmaceutical efficacy when applied locally. It has turned out that pharmaceutically suitable carriers coated with hedgehog protein should preferably contain a concentration of the hedgehog protein of 0.1–10 mg/ml carrier and more. Carriers are particularly advantageous which contain hedgehog proteins at a concentration of 0.1–10 mg/ml carrier or more.

Hedgehog proteins are inherently poorly soluble. It has, however, surprisingly turned out that the solubility of hedgehog proteins increases considerably, hedgehog proteins are protected from oxidation and the stability of hedgehog proteins is improved at low concentrations (1 mg/ml or less) in solutions which contain arginine or argininium ions (preferably argininium sulfate or argininium chloride). A further subject matter of the invention is therefore aqueous solutions of hedgehog proteins according to the invention at a concentration of 1 mg/ml and more which additionally contain arginine or argininium ions and are preferably buffered.

A further subject matter of the invention is a process for the production of a carrier matrix coated with hedgehog protein which is characterized in that the carrier matrix is incubated with a hedgehog protein solution according to the invention at a concentration of 1–10 mg/ml hedgehog protein which contains the additives according to the invention and arginine or argininium ions, preferably as argininium sulfate or argininium chloride, and the carrier matrix coated in this manner is isolated. Such solutions are suitable for producing carrier matrices which contain hedgehog proteins in pharmaceutically effective concentrations and are suitable for pharmaceutical applications. The concentration of arginine or argininium ions or argininium sulfate is preferably between 10 and 700 mmol/l, most preferably between 10 and 500 mmol/l, preferably in the pH range between 5 and 8, most preferably in the pH range between 6 and 8.

Activity within the sense of the invention is understood as the activity of alkaline phosphatase (stimulation of the expression of alkaline phosphatase) which the polypeptide can induce in mammalian cells (activity in the alkaline phosphatase test). In this method a mouse fibroblast cell line is cultured in a medium which contains fetal calf serum. Subsequently sterile filtered sample is added, the cells are lysed after about 5 days and alkaline phosphatase is determined in the cell lysate by means of the cleavage of a chromogenic substrate (pNP, p-nitrophenol) (J. Asahina, Exp. Cell. Res. 222 (1996) 38–47 and T. Nakamura (1997)).

A hedgehog protein is understood by the invention as a secreted signal protein which is responsible for the formation of numerous structures in embryogenesis. Sonic, indian or desert hh are particularly preferably used (Fietz M. et al., Development (Suppl.) (1994) 43–51). The processed form (N-terminal mature signal domain) of sonic hh protein (sequence: EMBL data bank, No. L38518) is preferably used. Proteins of the hedgehog family exhibit a pronounced homology in their amino acid sequence which is why it is also preferable to express those nucleic acids which code for hedgehog proteins which are 80% or more homologous to the above-mentioned sequence of sonic hedgehog protein. Hedgehog derivatives are preferably used that are described for example in the European Patent Applications No. 98102095.1 and 98107911.4.

The human sonic hedgehog precursor protein is composed of the amino acids 1–462 of the sequence described in the EMBL databank under No. L38518. The amino acids 1–23 represent the signal peptide, the amino acids 24–197 represent the mature signal domain, the amino acids 32–197 represent the signal domain shortened by eight amino acids and the amino acids 198–462 represent the autoprocessed C-terminal domain after autoproteolytic cleavage.

The composition according to the invention contains a pharmacologically effective dose of the hh protein and can be administered locally or systemically. It is preferable to use the proteins according to the invention in combination with other proteins of the hedgehog family or bone growth factors such as bone morphogenetic proteins (BMPs) (Wozney et al., Cell. Mol. Biol. of Bone, Bone Morphogenetic Proteins and their Gene Expression (1993) Academic Press Inc., 131–167) or parathyroid hormones (Karablis et al., Genes and Development 8 (1994) 277–289) or insulin-like growth factors (IGF-I or II) or transforming growth factor family (TGF-β, GDFs).

The composition according to the invention preferably contains a polymer which essentially acts as the structural substance which preferably also has an adhesion function for cells. Collagen is for example such a structural substance. In this case it is preferable that the structural substance is present at a lower concentration than the hydrophilic biocompatible carrier described by the invention.

Furthermore it is preferable for the production of the composition to add auxiliary substances such as sugars (mannitol, sucrose, lactose, glucose, trehalose, preferably 20–100 mg/ml) or amino acids such as glycine or arginine, methionine, cysteine as well as antioxidants such as citrate, thioglycerol, acetylcysteine, polyethylene glycol (1–10% by weight), detergents, preferably non-ionic detergents (preferably 0.01–0.1% by weight) such as polysorbates (Tween®20 or Tween®80) or polyoxyethylenes, anti-inflammatory agents, local anaesthetics, antibiotics and/or stabilizers such as lipids, fatty acids and glycerol.

In a further preferred embodiment a composition of the hedgehog protein according to the invention containing suramin is preferred and this can be used advantageously.

The composition can contain additional pharmaceutical auxiliary substances.

In a preferred embodiment the composition contains hedgehog protein at a concentration of 0.1–100 mg/ml.

In a preferred embodiment the composition additionally contains a pharmaceutically acceptable buffer which is biocompatible, preferably in the range between pH 3 and pH 10, particularly preferably in the range between pH 5 and 8. It has surprisingly turned out that the additives according to the invention are also able to effectively stabilize hedgehog proteins in the acidic range. The pH value of the composition should be advantageously greater than pH 4 in order to prevent denaturation and detachment of the zinc complexed in the hedgehog protein. The concentration of the buffer is preferably 1–500 mmol/l, in particular 5–150 mmol/l and particularly preferably 10–100 mmol/l. Examples of buffers which can be used in the pharmaceutical compositions of the present invention are arginine-chloride, argininium chloride and potassium phosphate. In the most preferred embodiments 300 mmol/l potassium phosphate buffer, pH 6.0 or 10 mmol/l potassium phosphate, 500 mmol/l arginine chloride, pH 6.0 is used with or without 0.01 to 0.5% Tween® 80, especially for hydrophobized, preferably palmitoylated hh proteins. Such hydrophobized hh proteins are described in U.S. Ser. No. 09/301,199 and in U.S. Ser. No. 09/198,975 which are incorporated herein by reference.

The following examples and publications further elucidate the invention, the protective scope of which results from the patent claims. The described methods are to be understood as examples which still describe the subject matter of the invention even after modifications.

EXAMPLE 1

DSC (differential scanning calorimetry) Analysis of Various Hedgehog Formulations Hedgehog protein solutions with a protein concentration of ca. 0.5 mg/ml were analysed in various buffers (50 mM HEPES-NaOH, pH 7.2 and 150 mM arginine-Cl, pH 7.4) with or without stabilizers by means of DSC (Nano Differential Scanning Calorimeter, Calorimetry Sciences Corporation, Utah, USA) at a heating rate of 2 K/min. The following stabilizers were used:

zinc acetate (Merck)
zinc sulfate (Merck)
heparin (low molecular weight, Sigma)
sulfated β-cyclodextrin (Aldrich)
arginine sulfate.

The transition temperatures (Tt) determined for the respective formulations are summarized in the table. It can be seen from the data shown that addition of the substances mentioned in the text increases the transition temperature and thus increases the stability of the hedgehog protein. The measured temperature values should not be understood as absolute values but rather represent differences in the stability of the individual formulations relative to one another.

Transition temperatures for hedgehog proteins in various formulations:

| Formulations | Tt [° C.] |
| --- | --- |
| 50 mM Hepes-NaOH, pH 7.2 | 52.0 |
| 50 mM Hepes-NaOH, 1 mM zinc acetate, pH 7.2 | 56.8 |
| 50 mM Hepes-NaOH, 1 mM zinc sulfate, pH 7.2 | 60.6 |
| 150 mM arginine chloride, pH 7.4 | 53.5 |
| 150 mM arginine chloride, 5% (w/v) sulfated β-cyclodextrin, pH 7.4 | 55.6 |
| 150 mM arginine chloride, 20 mg/ml heparin, pH 7.4 | 57.8 |
| 150 mM arginine sulfate, pH 6.0 | 63.4 |

EXAMPLE 2

Stability of Sonic Hedgehog at 37° C.

Human sonic hedgehog protein is incubated in various formulations at 37° C. Samples were taken at the stated times and analysed by means of rpHPLC.

Formulation A: PBS (10 mmol/l potassium phosphate, 150 mmol/l sodium chloride pH 7.4)

| Time [h] | Recovery [%] | shh oxidized [%] | shh native [%] |
|---|---|---|---|
| 0 | 100 | — | 78 |
| 1 | 104 | — | 44 |
| 5 | 173 | — | 68 |
| 24 | 134 | 71 | 29 |
| 48 | 140 | 76 | 24 |
| 72 | 142 | 84 | 16 |
| 96 | 39 | 79 | 21 |
| 168 | 31 | 79 | 21 |

Formulation B: 150 mM arginine-Cl, 0.01% Tween 80, pH 6.0

| Time [h] | Recovery [%] | shh oxidized [%] | shh native [%] |
|---|---|---|---|
| 0 | 100 | — | 79 |
| 1 | 100 | — | 75 |
| 5 | 93 | — | 81 |
| 24 | 108 | 40 | 60 |
| 48 | 139 | 45 | 55 |
| 72 | 144 | 58 | 42 |
| 96 | 124 | 76 | 24 |
| 168 | 118 | 86 | 14 |

It is clear that hshh in formulation B is more stable than in formulation A. The oxidation of shh is considerably slower in the formulation containing arginine and the recovery is higher since the temperature-induced aggregation of hshh is prevented.

EXAMPLE 3

Stability of Hydrophobically Modified shh at 37° C.

Human hydrophobically modified sonic hedgehog protein (palmitoylated shh, prepared accordiing to U.S. Ser. No. 09/301,199) is incubated in various formulations at 37° C. Samples are taken at various times and analysed by means of rpHPLC.

Formulation A: PBS (10 mmol/l potassium phosphate, 150 mmol/l sodium chloride, pH 7.4)

| Time [h] | Recovery [%] | shh native [%] |
|---|---|---|
| 0 | 100 | 91 |
| 1 | 81 | 80 |
| 5 | — | 84 |
| 24 | 74 | 70 |
| 48 | 25 | 47 |
| 72 | 31 | 40 |
| 96 | 4 | 0 |
| 168 | | 0 |

Formulation B: 150 mM arginine-Cl, 0.01% Tween 80, pH 6.0

| Time [h] | Recovery [%] | shh native [%] |
|---|---|---|
| 0 | 100 | 89 |
| 1 | 114 | 89 |
| 5 | 107 | 89 |
| 24 | — | 84 |
| 48 | 132 | 85 |
| 72 | 129 | 78 |
| 96 | 111 | 73 |
| 168 | 88 | 66 |

It is clear that hshh is more stable in formulation B than in formulation A. The recovery is higher since the temperature-induced aggregation of hshh is prevented.

EXAMPLE 4

Production of Pharmaceutical Compositions

Each of the compositions in the following table were formulated as a sterile filtered aqueous solution of 100 ml.

| Hshh* | Buffer | pH | Additive | Carrier |
|---|---|---|---|---|
| 5 mg/mg | 300 mmol/l potassium phosphate | 6 | 1 mmol/l zinc sulfate | |
| 5 mg/ml | 300 mmol/l potassium phosphate | 6 | 1 mmol/l zinc sulfate | |
| 5 mg/ml | 300 mmol/l potassium phosphate | 6 | 1 mmol/l magnesium acetate | |
| 5 mg/ml | 300 mmol/l potassium phosphate | 6 | 1 mmol/l calcium acetate | |
| 1 mg/ml | 300 mmol/l potassium phosphate | 6 | 5% w/v β-cyclodextrin sulfate | |
| 1 mg/ml | 300 mmol/l potassium phosphate | 6 | 10 mg/ml heparin | |
| 1 mg/ml | 150 mmol/l argininum chloride | 7.0 | 10 mg/ml heparin | |
| 1 mg/ml | 10 mmol/l potassium phosphate, 500 mmol/l argininium chloride | 6.0 | 0.1% (w/v) Tween ® 80 | |
| 5 mg/ml | 10 mmol/l potassium phosphate, 500 mmol/l argininium chloride | 6.0 | 0.1% (w/v) Tween ® 80 | |
| 10 mg/ml | 500 mmol/l argininium chloride, 10 mM potassium phosphate | 6.0 | 10 mg/ml heparin | 1% Na alginate |
| 10 mg/ml | 500 mmol/l argininium chloride, 10 mM potassium phosphate | 6.0 | 1 mmol/l calcium acetate | 10 mg/ml dextran sulfate |
| 10 mg/ml | 500 mmol/l argininium chloride, 10 mM potassium phosphate | 6.0 | 1 mmol/l calcium acetate | 10 mg/ml hyaluronic acid |

*human sonic hedgehog protein (palmitoylated)

a) Compositions Without Carrier

For each of the compositions in the table above, hedgehog protein and additive are added to 100 ml solution of buffer and water. The solution is stirred, sterile filtered, and stored at 4° C. 0.5 to 2.0 ml of the solution is administered by injection to a human patient.

b) Compositions With Carrier

Compositions containing a carrier are separately formulated by stirring the hedgehog protein, buffer and additive solution with hyaluronic acid, sodium alginate or dextran sulfate solution (1% w/v) to form a gelatinous mixture. This gel can be either used directly as an injectable matrix or further processed into capsules or stored as a lyophilisate.

List of References

Asahina, J., Exp. Cell. Res. 222 (1996) 38–47
Bitgood, M. J. et al., Curr. Biol. 6 (1996) 298–304
Chiang, C. et al., Nature 83 (1996) 407
European Patent Application No. 98102095.1
European Patent Application No. 98107911.4
Fietz, M. et al., Development (Suppl) (1994) 43–51
Hynes, M. et al., Neuron 15 (1995) 35–44
Karablis et al., Genes and Development 8 (1994) 277–289
Kinto et al., FEBS Letters, 404 (1997) 319–323
Lai, C. J. et al., Development 121 (1995) 2349
Lopez-Martinez et al. in Curr.Biol. 5 (1995) 791–796
Marti et al., Nature 375 (1995) 322–325
Miao et al., J. Neurosci. 17 (1997) 5891–5899
Nakamura, T. et al., Biochem. Biophys. Res. Comm. 237 (1997) 465–469
Pepinski et al., J. Biol. Chem. 273 (1998) 14037–14045
Perrimon, N., Cell 80 (1995) 517–520
Porter, J. A. et al., Science 274 (1996) 255–259
Smith, J. C., Cell 76 (1994) 193–196
Stott et al., J. Cell Sci. 110 (1997) 2691–2701
U.S. Ser. No. 09/198,975
U.S. Ser. No. 09/301,199
Vortkamp, A. et al., Science 273 (1996) 613
Wozney et al., Cell. Mol. Biol. of Bone, Bone Morphogenetic Proteins and their Gene Expression, (1993) Academic Press Inc. 131–167
Yang et al., Development 124 (1997) 4393–4404

What is claimed is:

1. A composition adapted for formulating unit dosage forms for administration to a patient wherein said composition comprises an aqueous solution containing a hedgehog protein; and an additive being present in an effective amount to stabilize said hedgehog protein in the aqueous solution, wherein said additive is selected from the group consisting of ionic salts, cyclodextrin, non-ionic detergent, anionic saccharide and mixtures thereof, said ionic salt containing an ion selected from the group consisting of zinc, sulfur, magnesium, calcium, arginine, argininium and mixtures thereof.

2. The composition according to claim 1, wherein said hedgehog protein is present in the composition in an amount from about 0.1 mg/ml to about 100 mg/ml.

3. The composition according to claim 1 or 2, wherein said hedgehog protein is palmitoylated.

4. The composition according to claim 1, wherein the additive is an anionic saccharide selected from the group consisting of chondroitin sulfate and heparin.

5. The composition according to claim 1, wherein the additive is polyoxysorbate.

6. The composition according to claim 1, wherein the additive is cyclodextrin sulfate.

7. The composition according to claim 1, wherein the additive is argininium sulfate.

8. The composition according to claim 1, wherein the composition contains a molar excess of the additive relative to the amount of the hedgehog protein.

9. The composition according to claim 8, wherein the additive is present in an amount of from about 1 to about 1000 fold greater than the amount of hedgehog protein.

10. The composition according to claim 9, wherein the additive is present in an amount of from about 1 to about 100 fold greater than the amount of the hedgehog protein.

11. The composition according to claim 1, wherein the additive is an ionic salt, said ionic salt being present in the composition at a concentration of from about 0.01 mmol/l to about 500 mmol/l.

12. The composition according to claim 1, wherein the additive is cyclodextrin, said cyclodextrin being present in the composition at a concentration of from about 1% to about 20% by weight of said composition.

13. The composition according to claim 1, wherein the additive is a non-ionic detergent, said non-ionic detergent being present in the composition at a concentration of from about 0.01% to about 0.1% of said composition.

14. The composition according to claim 1, wherein the additive is an ionic salt containing arginine or an argininium ion, said arginine or argininium ion being present in the composition at a concentration of about 10 mmol/l to about 700 mmol/l.

15. The composition according to claim 1, wherein the hedgehog protein is bound to a biocompatible carrier.

16. The composition according to claim 1, wherein the biocompatible carrier is hydrophilic.

17. The composition according to claim 15, wherein the hydrophilic carrier is a polymer.

18. The composition according to claim 1, wherein the composition is buffered in a range of from about pH 3 to about pH 10.

19. The composition according to claim 1, wherein the composition is lyophilized.

* * * * *